(12) United States Patent
Racicot et al.

(10) Patent No.: US 8,603,411 B2
(45) Date of Patent: Dec. 10, 2013

(54) POLYMER MATERIAL AND SEALS FORMED THEREOF FOR HIGH PRESSURE PUMP APPLICATIONS

(71) Applicants: Robert Thomas Racicot, Murrieta, CA (US); Jon M. Lenhert, Brea, CA (US); Karthik Vaideeswaran, Redondo Beach, CA (US); Christopher M. Comeaux, Worcester, MA (US)

(72) Inventors: Robert Thomas Racicot, Murrieta, CA (US); Jon M. Lenhert, Brea, CA (US); Karthik Vaideeswaran, Redondo Beach, CA (US); Christopher M. Comeaux, Worcester, MA (US)

(73) Assignee: Saint-Gobain Performance Plastics Corporation, Aurora, OH (US)

( * ) Notice: Subject to any disclaimer, the term of this patent is extended or adjusted under 35 U.S.C. 154(b) by 0 days.

(21) Appl. No.: 13/709,888

(22) Filed: Dec. 10, 2012

(65) Prior Publication Data

US 2013/0170980 A1 Jul. 4, 2013

Related U.S. Application Data

(62) Division of application No. 12/647,002, filed on Dec. 24, 2009, now Pat. No. 8,349,959.

(60) Provisional application No. 61/140,760, filed on Dec. 24, 2008.

(51) Int. Cl.
| | | |
|---|---|---|
| *F16J 15/32* | (2006.01) | |
| *F16J 15/18* | (2006.01) | |
| *F16J 15/16* | (2006.01) | |
| *F04B 53/18* | (2006.01) | |

(52) U.S. Cl.
USPC ........... 422/500; 422/255; 525/199; 525/200; 524/520

(58) Field of Classification Search
USPC ............ 422/500, 255; 525/199, 200; 524/520
See application file for complete search history.

(56) References Cited

U.S. PATENT DOCUMENTS

| | | | |
|---|---|---|---|
| 2,168,818 A | 8/1939 | Condon | |
| 4,050,701 A | 9/1977 | Webb | |
| 4,163,742 A | 8/1979 | Mansure | |
| 4,333,977 A | 6/1982 | Abrahams et al. | |
| 4,502,694 A | 3/1985 | Uhrner | |
| 4,703,076 A | 10/1987 | Mori | |
| 4,706,970 A | 11/1987 | Ramirez | |
| 4,721,312 A | 1/1988 | Hornberger | |
| 4,735,144 A | 4/1988 | Jenkins | |
| 4,749,752 A | 6/1988 | Youlu et al. | |
| 4,750,748 A | 6/1988 | Visser | |
| 4,804,290 A | 2/1989 | Balsells | |
| 4,819,443 A | 4/1989 | Watanabe et al. | |
| 4,907,788 A | 3/1990 | Balsells | |
| 5,144,882 A | 9/1992 | Weissgerber | |
| 5,444,116 A * | 8/1995 | Amin et al. | ............ 524/495 |
| 5,494,300 A | 2/1996 | Tanaka et al. | |
| 5,575,634 A | 11/1996 | Tanaka et al. | |
| 5,671,656 A | 9/1997 | Cyphers et al. | |
| 5,763,082 A | 6/1998 | Kokumai et al. | |
| 5,767,186 A | 6/1998 | Shimokusuzono et al. | |
| 5,985,949 A | 11/1999 | Seguchi et al. | |
| 5,992,856 A | 11/1999 | Balsells et al. | |
| 6,025,440 A | 2/2000 | Scheckenbach et al. | |
| 6,204,301 B1 | 3/2001 | Oshima et al. | |
| 6,310,141 B1 | 10/2001 | Chen et al. | |
| 6,340,718 B1 | 1/2002 | Korenev et al. | |
| 6,341,384 B1 | 1/2002 | Hayes | |
| 6,376,109 B1 | 4/2002 | Sano et al. | |
| 6,419,236 B1 | 7/2002 | Janian | |
| 6,465,575 B1 | 10/2002 | Kusano et al. | |
| 6,552,099 B2 | 4/2003 | Yamamoto et al. | |
| 6,749,649 B2 | 6/2004 | Sano et al. | |
| 6,884,827 B2 | 4/2005 | Ota et al. | |
| 6,918,595 B2 | 7/2005 | Proper | |
| 7,342,072 B2 | 3/2008 | Park et al. | |
| 7,640,841 B2 * | 1/2010 | An et al. | ............ 92/168 |
| 7,802,796 B2 * | 9/2010 | Racicot | ............ 277/500 |
| 2001/0039966 A1 | 11/2001 | Walpole et al. | |
| 2002/0086191 A1 | 7/2002 | Sano et al. | |
| 2002/0090537 A1 | 7/2002 | Sano et al. | |
| 2002/0153664 A1 | 10/2002 | Schroeder | |
| 2002/0155289 A1 | 10/2002 | Cistone et al. | |
| 2003/0085532 A1 | 5/2003 | Spiegl et al. | |
| 2003/0085533 A1 | 5/2003 | Spiegl et al. | |
| 2003/0111798 A1 | 6/2003 | Yanagiguchi et al. | |
| 2003/0125466 A1 | 7/2003 | Chmielewski | |
| 2003/0144156 A1 | 7/2003 | Saito | |
| 2004/0056430 A1 | 3/2004 | Lineton | |
| 2004/0082701 A1 | 4/2004 | Ota et al. | |
| 2004/0208406 A1 | 10/2004 | Budde et al. | |
| 2005/0106970 A1 | 5/2005 | Stanitis et al. | |
| 2005/0121437 A1 | 6/2005 | Spohn et al. | |
| 2005/0189725 A1 | 9/2005 | Edwards | |
| 2005/0221038 A1 | 10/2005 | Park | |
| 2007/0176372 A1 | 8/2007 | Racicot | |
| 2007/0180987 A1 | 8/2007 | An et al. | |
| 2009/0202769 A1 | 8/2009 | Masuda et al. | |

FOREIGN PATENT DOCUMENTS

| | | |
|---|---|---|
| EP | 0202996 A2 | 11/1986 |
| EP | 0850993 A1 | 7/1998 |
| EP | 0874023 A1 | 10/1998 |
| EP | 0583481 B1 | 11/1999 |
| EP | 0739046 B1 | 3/2000 |

(Continued)

OTHER PUBLICATIONS

International Search Report for PCT/US2009/069521 dated Aug. 13, 2010, 4 pgs.

(Continued)

*Primary Examiner* — Nathan M Nutter

(74) *Attorney, Agent, or Firm* — Chi Suk Kim; Abel Law Group, LLP

(57) ABSTRACT

A seal is formed of a material including a crosslinked fluoropolymer. The seal substantially prevents leaks in a high pressure pump.

14 Claims, 3 Drawing Sheets

(56) References Cited

FOREIGN PATENT DOCUMENTS

| EP | 0916044 B1 | 4/2003 |
|---|---|---|
| EP | 1584645 A1 | 10/2005 |
| EP | 1739305 A1 | 1/2007 |
| JP | 61-169231 A | 7/1986 |
| JP | 62-105623 A | 5/1987 |
| JP | 62-146944 | 6/1987 |
| JP | 3-273083 A | 12/1991 |
| JP | 6-340866 A | 12/1994 |
| JP | 07-062184 | 3/1995 |
| JP | 7-268126 A | 10/1995 |
| JP | 8-105391 A | 4/1996 |
| JP | 10-237301 | 9/1998 |
| JP | 10-237421 | 9/1998 |
| JP | 2001-115976 | 4/2001 |
| JP | 2001-181603 | 7/2001 |
| JP | 2005299808 A | 10/2005 |
| WO | 96/40857 | 12/1996 |
| WO | 99/11355 | 3/1999 |
| WO | 01/06881 A1 | 2/2001 |
| WO | 01/18289 A1 | 3/2001 |
| WO | 02/20886 A1 | 3/2002 |
| WO | 02/43881 A1 | 6/2002 |
| WO | 2005/056647 A2 | 6/2005 |
| WO | 2005/064212 A2 | 7/2005 |
| WO | 2005119103 A1 | 12/2005 |

OTHER PUBLICATIONS

Mark P. Wolverton et al.; "Tribological Properties of Reinforced and Lubricated Thermoplastic Composites at Elevated Temperatures"; Session 15-B, pp. 1-8; Feb. 7-11, 1983.

Kevin Yu et al.; "Wear Tests of Polymer Composite Compressor Seal Materials in Hydrogen Environment"; Paper No. 52; Copyright 1999 by NACE International.

"Buckyballs, Diamond, and Graphite"; on-line, BDG Graphite and Carbon Fibers; pp. 1-13; Dec. 22, 2005.

"Dyneon TFM PTFE, Improved performance and design flexibility"; on-line, pp. 1-20; Copyright Dyneon 2002.

* cited by examiner

POLYMER MATERIAL AND SEALS FORMED THEREOF FOR HIGH PRESSURE PUMP APPLICATIONS

CROSS-REFERENCE TO RELATED APPLICATIONS

The present application is a divisional application of U.S. patent application Ser. No. 12/647,002, filed Dec. 24, 2009 and entitled "POLYMER MATERIAL AND SEALS FORMED THEREOF FOR HIGH PRESSURE PUMP APPLICATIONS," naming inventors Robert T. Racicot, Jon M. Lenhert, Karthik Vaideeswaran, and Christopher Comeaux which claims priority to U.S. Provisional Patent Application No. 61/140,760, filed Dec. 24, 2008, entitled "POLYMER MATERIAL AND SEALS FORMED THEREOF FOR HIGH PRESSURE PUMP APPLICATIONS," naming inventors Robert T. Racicot, Jon M. Lenhert, Karthik Vaideeswaran, and Christopher Comeaux, which applications are incorporated by reference herein in their entirety.

FIELD OF THE DISCLOSURE

This disclosure, in general, relates to polymer materials and seals formed thereof.

BACKGROUND

Traditionally, seals are used to prevent fluids from flowing between joints of rigid components. In particular examples, seals are used in pumps and between flanges to limit fluid flow out of containment regions. For example, seals along pump shafts may limit lubricating fluids or pressurized process fluids from escaping along an annulus defined by the shaft and a housing. Traditionally, such seals have been formed of malleable materials, such as graphite or metal strips in the case of flange seals or elastomeric materials in the case of shaft seals. However, traditional materials have proven ill suited for new applications, such as high pressure liquid chromatography systems.

High pressure rod actuated pumps such as high pressure liquid chromatography uses a high pressure liquid carrier medium to separate chemical species by moving the species across an adsorption medium. Different chemical components adsorb on and desorb from the adsorption medium at different rates resulting in separation of the components as the carrier medium moves through or around the adsorption medium. Accordingly, the effectiveness of a high pressure chromatography system may be adversely influenced by extraneous ions or particulate materials in the carrier medium. As such, new materials are being used in the formation of pumps and other components of high pressure liquid chromatography pumps. Traditional sealing components using traditional sealing materials have been shown to damage pump components formed of the new materials compatible with liquid chromatography systems or have been shown to release undesirable ions or particulate materials into the liquid carrier medium, which reduce the effectiveness of high pressure liquid chromatography systems. In particular, traditional sealing materials may scratch pump shafts, damaging expensive pump components and shortening the lifespan of pumps. In another example, the traditional sealing material may release particulate material into the liquid carrier medium clogging the liquid chromatography column and reducing the effectiveness of the high pressure liquid chromatography system. In particular examples, the particulate material may act as an additional adsorption surface, adversely influencing the separation of chemical components.

As such, an improved seal material would be desirable.

SUMMARY

In a particular embodiment, a seal is formed of a material including a crosslinked fluoropolymer, wherein the seal substantially prevents leaks in a high pressure pump.

In another exemplary embodiment, a pump includes a rod and a seal. The seal includes a surface in contact with the rod. The seal is formed of a material comprising a crosslinked fluoropolymer.

BRIEF DESCRIPTION OF THE DRAWINGS

The present disclosure may be better understood, and its numerous features and advantages made apparent to those skilled in the art by referencing the accompanying drawings.

DESCRIPTION OF THE PREFERRED EMBODIMENTS

Figure 1:
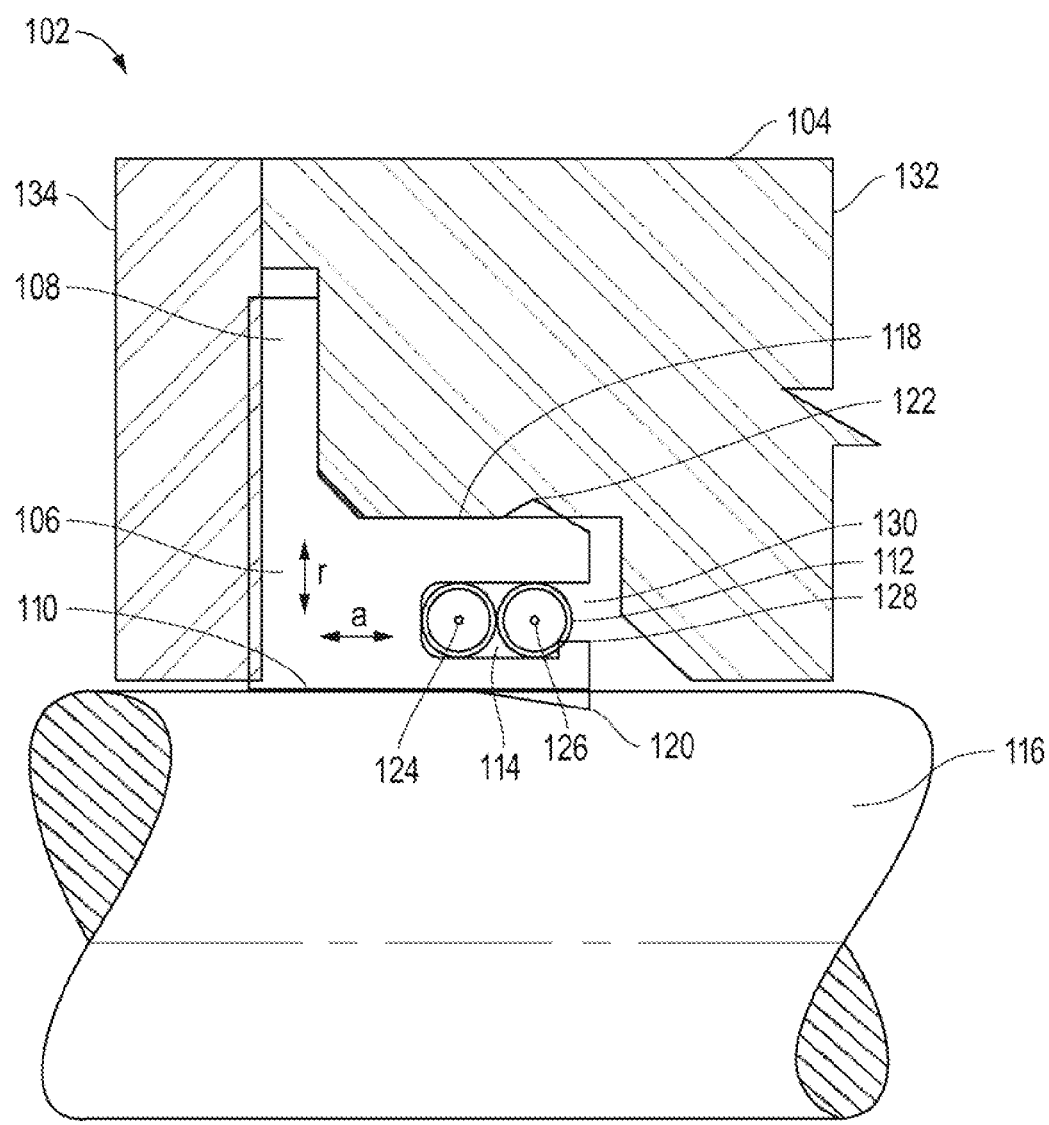
FIG. 1 includes an illustration of a portion of an exemplary pump in which a seal formed of the disclosed seal material may be used.

In a particular embodiment, a seal is formed of a material including a crosslinked fluoropolymer. In an embodiment, the material includes a fluoropolymer blend. In a particular embodiment, the material includes a blend of a crosslinked fluoropolymer with a non-crosslinked fluoropolymer. The seal is particularly useful for high pressure pump applications. "High pressure" as used herein includes pressures of up to about 120 MPa. In a particular embodiment, the pump is a high pressure liquid chromatography pump. In particular, the seal may be formed in annular configuration for use in a pump with a rod extending through the center of the seal.

In an embodiment, the material forming the seal includes a crosslinked fluoropolymer. In an exemplary embodiment, the material includes a polymer matrix formed of a fluoropolymer. An exemplary crosslinked fluoropolymer includes a polymer formed from a fluorine substituted olefin monomer or a polymer including at least one monomer selected from the group consisting of vinylidene fluoride, vinylfluoride, tetrafluoroethylene (TFE), hexafluoropropylene, trifluoroethylene, chlorotrifluoroethylene, perfluorovinylethers, or a mixture of such fluorinated monomers. An exemplary perfluorovinylether includes, for example, perfluoro(alkylvinylether) [PFAVE] or perfluoro(alkoxyalkylvinylether). An exemplary crosslinked fluoropolymer may include a polymer, a polymer blend or a copolymer including one or more of the above monomers, such as, for example, fluorinated ethylene propylene (FEP), ethylene-tretrafluoroethylene (ETFE), poly tetrafluoroethylene-perfluoropropylvinylether (PFA), poly tetrafluoroethylene-perfluoromethylvinylether (MFA), polytetrafluoroethylene (PTFE), polyvinylidene fluoride (PVDF), ethylene chlorotrifluoroethylene (ECTFE), polychlorotrifluoroethylene (PCTFE), tetrafluoroethylene-hexafluoropropylene-vinylidene fluoride (THV), and the like. In an embodiment, the polytetrafluoroethylene (PTFE) may be a modified PTFE. In an example, the modified PTFE is a copolymer of tetrafluoroethylene and a vinyl ether, such as perfluoropropylvinylether (PPVE). In an embodiment, the modified PTFE includes at least about 0.01 wt % perfluoropropylvinylether (PPVE). In another example, the modified PTFE includes not greater than about 5.0 wt % PPVE, such as not greater than about 3.0 wt % or not greater than about 1.5 wt % PPVE.

The polymer, polymer blend, or a copolymer including one or more of the above monomers may be crosslinked by applying ionizing radiation to the fluoropolymer. In an embodiment, the fluoropolymer is heated under an inert gas atmosphere having an oxygen concentration of 10 Torr or less within a range of an irradiation dose of about 1 KGy to about 10 MGy. An example of the ionizing radiation includes gamma rays, electron rays, X rays, neutron radiation and high-energy ions, and the like. In an embodiment, thermal treatment may occur in combination with ionization radiation.

Thermal treatment may be used to facilitate crosslinking of the fluoropolymer. In an exemplary embodiment, thermal treatment includes heating the fluoropolymer to a temperature at its crystalline melting point or a higher temperature. Heating the fluoropolymer activates molecular motion of backbone chains, which constitute the fluoropolymer, whereby crosslinking reactions among molecules are efficiently activated. However, excessive heating brings about decomposition of the molecular backbone chains of the fluoropolymer. Accordingly, a heating temperature is typically not greater than about 30° C., such as not greater than about 10° C. higher than the melting point of the fluoropolymer in order to suppress any occurrence of such a depolymerizing phenomenon. In an embodiment, when PTFE is used as a fluoropolymer material, crosslinking may occur by exposing the PTFE to a heating condition at a temperature of at least about 327° C. or a higher temperature, i.e. at the melting point of the PTFE. In the case of employing a PFA, the PFA may be heated at its melting point of about 310° C. or a higher temperature. In the case of employing a FEP, the FEP may be heated at its melting point of about 275° C. or a higher temperature.

In an embodiment, the material forming the seal includes a crosslinked fluoropolymer and a non-crosslinked fluoropolymer. A non-crosslinked fluoropolymer, as used herein refers to a fluoropolymer that has not been exposed to heat, irradiation, or a combination thereof to form crosslinking reactions among the molecules of the fluoropolymer. An exemplary non-crosslinked fluoropolymer includes a polymer formed from a fluorine substituted olefin monomer or a polymer including at least one monomer selected from the group consisting of vinylidene fluoride, vinylfluoride, tetrafluoroethylene (TFE), hexafluoropropylene, trifluoroethylene, chlorotrifluoroethylele, or a mixture of such fluorinated monomers. An exemplary non-crosslinked fluoropolymer may include a polymer, a polymer blend or a copolymer including one or more of the above monomers, such as, for example, fluorinated ethylene propylene (FEP), ethylene-tretrafluoroethylene (ETFE), poly tetrafluoroethylene-perfluoropropylvinylether (PFA), poly tetrafluoroethylene-perfluoromethylvinylether (MFA), polytetrafluoroethylene (PTFE), polyvinylidene fluoride (PVDF), ethylene chlorotrifluoroethylene (ECTFE), polychlorotrifluoroethylene (PCTFE), tetrafluoroethylene-hexafluoropropylene-vinylidene fluoride (THV), or the like. In a particular embodiment, the non-crosslinked fluoropolymer is polytetrafluoroethylene (PTFE). In an embodiment, the polytetrafluoroethylene (PTFE) may be a modified PTFE. In an example, the modified PTFE is a copolymer of tetrafluoroethylene and a vinyl ether, such as perfluoropropylvinylether (PPVE). In an embodiment, the modified PTFE includes at least about 0.01 wt % perfluoropropylvinylether (PPVE). In another example, the modified PTFE includes not greater than about 5.0 wt % PPVE, such as not greater than about 3.0 wt % or not greater than about 1.5 wt % PPVE.

When the material includes a blend of the crosslinked fluoropolymer and the non-crosslinked fluoropolymer, the blend is at a ratio of about 10 wt % to about 90 wt %, such as about 20 wt % to about 80 wt %, such as about 30 wt % to about 70 wt %, or even about 50 wt % to about 50 wt %.

Additionally, the seal material can include one or more fillers, reinforcing agents, additives, and/or pigments, to provide certain desired seal performance properties, such as mechanical strength, lubricity, thermal and/or electrical conductivity, wear resistance, or appearance, i.e., color. It will be appreciated that the proportion of fillers and/or pigments within the seal material can vary depending on the fluoropolymer material selected for the seal.

In an embodiment, the material may include any number of additives to impart aesthetics like color etc. or to enhance specific properties like creep, temperature resistance, wear etc. Such additives may include catalysts, carriers, colorants, and the like or fillers including (but not limited to), glass, virgin polymers, irradiated polymers, glass, carbon, graphite, minerals, ceramics and metals and the like in flake, powder, fiber or other forms.

When present, the material may include filler at an amount of up to about 50 wt %, such as about 0 wt % to about 50 wt %, such as about 0 wt % to about 25 wt % of the total weight of the material. In an embodiment, the material may include filler at an amount of at least about 15 wt % of the total weight of the material. In an embodiment, the material may include polymer filler of up to about 50 wt % by weight of the total weight of the material. In an embodiment, the material may include conventional filler of about 0 wt % to about 25 wt % of the total weight of the material. In an embodiment, the material is substantially free of filler. "Substantially free" as used herein refers to a material that has less than about 0.1 wt % of the total weight of the material.

In an embodiment, the material is processed. Processing includes sintering the material by any methods known in the art, curing (i.e. to provide a chemical reaction), or any combination thereof. Any known method of curing the material is envisioned.

In an embodiment, the material of the seal may be crosslinked and available as finished stock sheets, rods, or the like. The crosslinked fluoropolymer may then be machined to provide the seal structure. In an embodiment, the blend of the crosslinked fluoropolymer and the non-crosslinked fluoropolymer are in the form of a molding powder. The crosslinked fluoropolymer and non-crosslinked fluoropolymer may be blended in accordance with the properties desired for the final molded product. In an embodiment, the molding powder can be advantageously molded to provide the seal structure. Molding may include, for example, compression molding, ram extrusion molding, isostatic molding, and the like.

In a particular embodiment, the seal formed of the material may be used in an annular configuration in a pump. FIG. 1 includes an illustration of a portion 102 of an exemplary pump. The portion 102 includes a rigid body 104 surrounding a rod 116. In a particular example, the rod 116 is formed of a hard, anti-wear surface. In an embodiment, the rod 116 includes hard, anti-wear surfaces such as sapphire, silicon carbide, zirconia, DLC (diamond-like-carbon) coated substrates, and the like. The rigid body 104 may include sections 132 and 134 configured to engage a seal body 106. Single or multiple springs may be used to obtain optimum sealing performance.

The seal body 106 formed of the exemplary material forms an annular sealing surface 110 that is configured to contact the rod 116. The seal body 106 also may form a second annular sealing surface 118 that is configured to contact the rigid body 104. An annular sealing surface is a sealing surface that extends axially and circumferentially around an annular body, such as the seal body 106. For example, annular sealing surface 110 forms a radially innermost surface of the seal body 106 and defines a bore through which the rod 116 may be inserted. In a particular embodiment, the seal 106 has an annular configuration having a minimum inner diameter of about 1 mm. Typically, the maximum diameter of the seal 106 is dictated by the dimensions of the rod/pump/unit. In another example, annular sealing surface 118 forms a radially outermost sealing surface configured to contact a pump housing. In an exemplary embodiment, the seal 106 includes a flange portion 108 which may act to form additional sealing surfaces or may be used to secure the seal 106. The seal body may also include annular ridges, such as annular ridges 120 and 122 protruding from the annular sealing surfaces 110 and 118, respectively. As illustrated in FIG. 1, ridges and edges are shown in a precompressed form to illustrate the form of the seal body prior to distortion by compression between the rod 116 and the housing 104.

In addition, the seal 106 includes a cavity 114 in which at least one spring 112 is situated. Typically, the pump may include one spring 112 although any reasonable configuration with greater than one spring is envisioned. Further, the spring 112 may be metallic or polymeric. In an embodiment, the polymeric spring may be elastomeric. In an embodiment, the seal 106 includes at least two annular springs 112 situated axially adjacent to each other and annularly surrounding the rod 116. In a particular embodiment, a peak of the annular ridge 120 is axially spaced apart from the central axes (124 and 126) of each of the annular springs 112. The seal body 106 defines an opening 130 to the cavity 114 at one axial end. The seal body may further include an annular lip 128 located on one side of the opening 130.

In an exemplary embodiment, the material may exhibit desirable mechanical and surface properties. For example, the material may exhibit desirable wear, as measured by a thrust-washer test and in accordance with ASTM D3702. Wear can be expressed with the mathematical equation:

$$W = K \cdot P \cdot V \cdot T$$

where W=Wear (inches), K=Wear Factor (in$^3$-min/lb-ft-hr), P=Pressure (lb/in$^2$), V=Surface Velocity (ft/min), and T=Elapsed Time (hours). In a particular embodiment, the material may have a wear of less than about 1000, such as less than about 500, such as less than about 100, or even less than about 50, expressed in $10^{-8}$ mm$^3$/Nm.

Particular embodiments of seals formed of the disclosed material advantageously exhibit desirable sealing properties. For example, embodiments advantageously exhibit low wear damage to and scratching of sapphire pump rods. Further, embodiments advantageously exhibit low release of particulate material to liquid carrier media. Furthermore, the material when formed into a seal may exhibit desirable resistance to degradation when exposed to liquid carrier media, such as de-ionized water, methanol, or a blend of phosphoric buffer solution and methanol. In an embodiment, the seal material substantially prevents leaks. In particular, seals formed of the composite material may operate at least about 300 hours without a leak failure when exposed to a liquid carrier medium. Liquid carrier mediums include, for example, any suitable medium for high pressure liquid chromatography such as de-ionized water, methanol, or a blend of phosphoric buffer solution and methanol. In a particular embodiment, the seal substantially prevents leaks at a pressure of about 70 MPa and higher with variable flow rates, such as at a pressure of about 100 MPa with variable flow rates, such as a flow rate of about 5 ml/min. In an embodiment, the seal substantially prevents leaks at a pressure of up to about 120 MPa at variable flow rates. Further, the material has an improved leakage rate compared to non-crosslinked fluoropolymers.

EXAMPLES

Example 1

Blends are made with modified PTFE and crosslinkable PTFE powder in ratios of about 80-20; 70-30 and 50-50. The blends are filled with one or more of boron nitride, carbon fibers, bronze, graphite fibers in addition to other fillers. The blends are compared to non-crosslinked modified PTFE (without crosslinkable PTFE powder).

Wear tests are performed in accordance with ASTM D3702. For wear tests done using such a method, the 50-50 (modified PTFE plus cross-linkable PTFE powder) blend shows substantially better results than non-crosslinked PTFE or modified PTFE. The wear rate of the 50-50 blend of a modified PTFE plus cross-linkable PTFE powder is seen to be several orders of magnitude better than these virgin grades. High speed rotary tests confirm this finding as well.

Creep resistance is tested at higher temperatures in accordance with ASTM-2990. For tests done up to 72 hours, the creep in compression is improved by a factor of 2 for the 50-50 blend of a modified PTFE plus cross-linkable PTFE powder compared to a non-crosslinked modified PTFE.

Example 2

Figure 2:
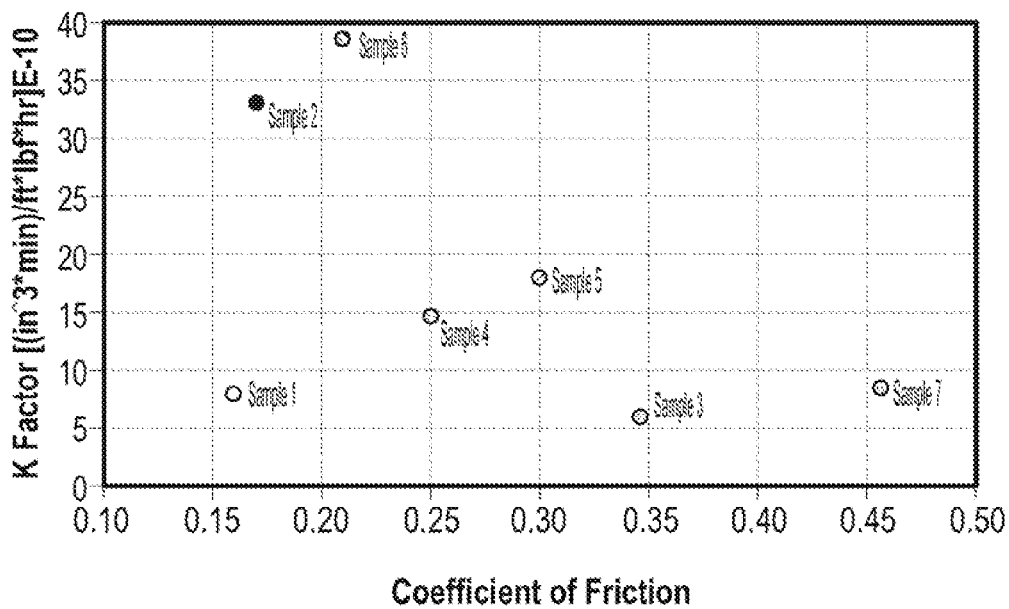
FIGS. 2, 3 and 4 include graphical illustrations of physical properties for embodiments of the disclosed seal material.
Figure 3:
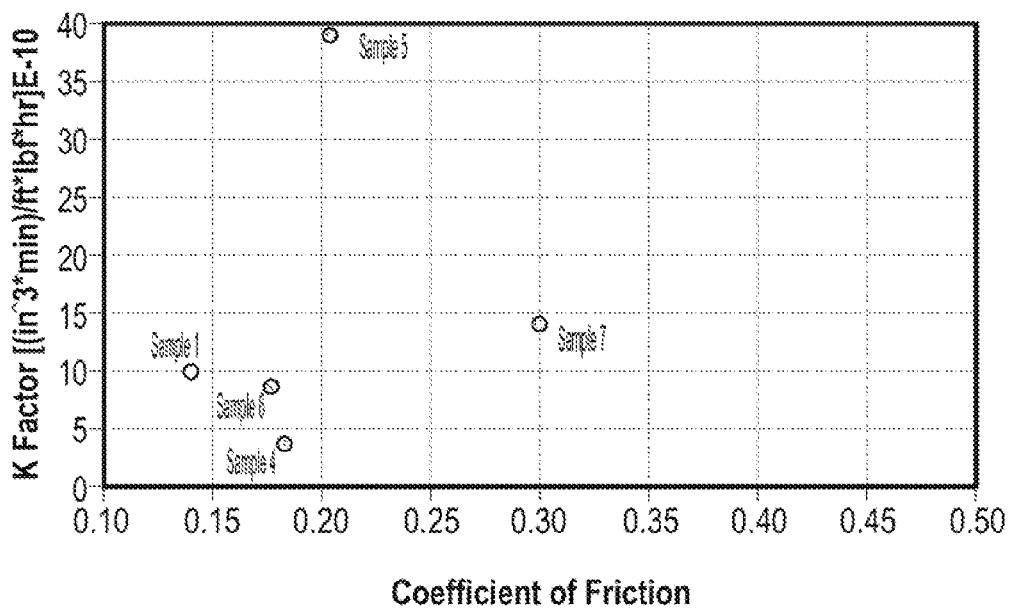

Wear and tribological properties are tested for the following materials.
Sample 1 and 2=Crosslinked PTFE and blends thereof.
Sample 3=Glass filled PTFE/modified PTFE
Sample 4=Polymer filled PTFE/modified PTFE
Sample 5=Mineral filled PTFE/modified PTFE
Sample 6=Carbon filled PTFE/modified PTFE
Sample 7=Standard material found in market The materials above are tested using an ASTM D3072 thrust washer test. The test conditions for the materials are 100 fpm and 0.7 MPa (as seen in FIG. 2) and 100 fpm and 2.8 MPa (as seen in FIG. 3). The results demonstrate that the crosslinked PTFE (Sample 1) is able to achieve low K factor (wear), without an increase in coefficient of friction (COF). Typically, fillers in a material such as PTFE will raise the coefficient of friction.

Results for mechanical/physical testing can be seen in Table 1. Testing standards are in accordance with ASTM D3702.

TABLE 1

| Designation | Tensile (MPa) | Elongation (%) | Specific Gravity |
|---|---|---|---|
| Sample 1 | 20 | 330 | 2.2 |
| Sample 2 | 16 | 245 | 2.1 |

Example 3

Three samples are tested for leakage rate in a simulated lab-level HPLC like application. The leakage rate around a seal and a reciprocating shaft (1 Hz reciprocation rate) is tested in a pressure chamber at a pressure of about 100 MPa for a period of about 2 weeks. The samples and average results can be seen in FIG. 4.

Figure 4:
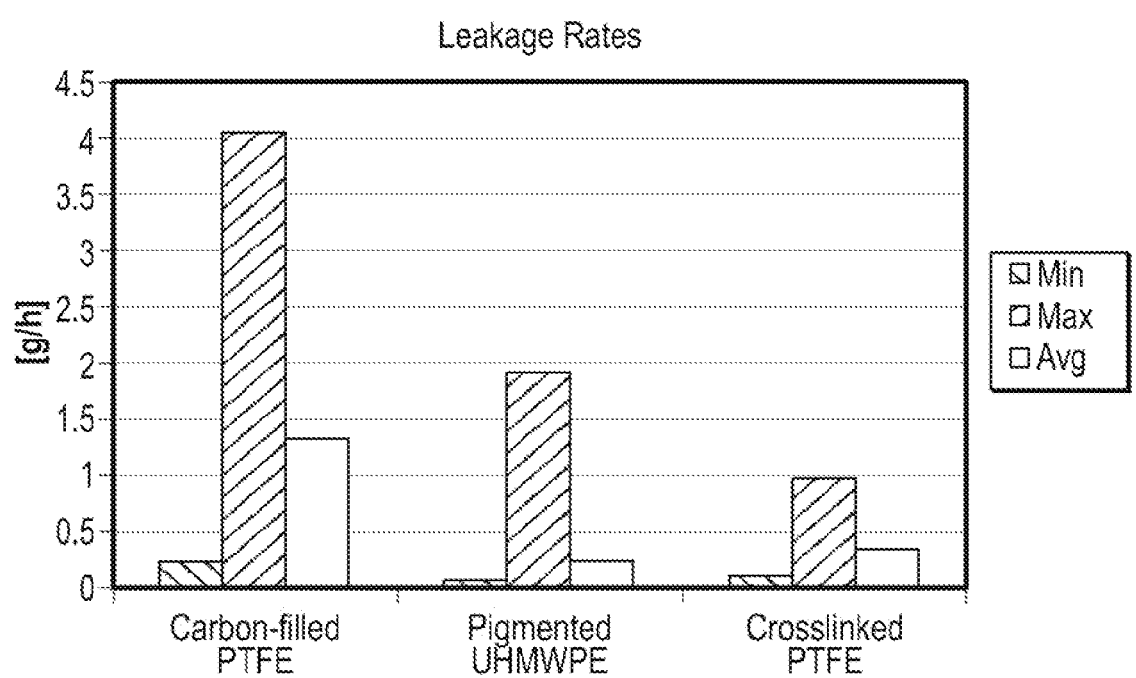

As seen in FIG. 4, the crosslinked PTFE has a leakage rate comparable to pigmented ultrahigh molecular weight polyethylene (UHMWPE). However, PTFE has improved chemical resistance compared to polyethylene, which is limited in its solvent compatibility. Further, the crosslinked PTFE has an improved leakage rate compared to carbon-filled PTFE.

The above-disclosed subject matter is to be considered illustrative, and not restrictive, and the appended claims are intended to cover all such modifications, enhancements, and other embodiments, which fall within the true scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. A pump comprising:
   a rod; and
   a seal including a surface in contact with the rod, wherein the seal is formed of a material comprising a crosslinked fluoropolymer.

2. The pump of claim 1, wherein the rod comprises a hard anti-wear surface.

3. The pump of claim 1, wherein the surface forms an annular surface around the rod.

4. The pump of claim 3, wherein the annular configuration has a minimum inner diameter of about 1 mm.

5. The pump of claim 1, wherein the crosslinked fluoropolymer comprises polytetrafluoroethylene.

6. The pump of claim 1, wherein the material further comprises a non-crosslinked fluoropolymer to form a fluoropolymer blend.

7. The pump of claim 6, wherein the blend of the crosslinked fluoropolymer and the non-crosslinked fluoropolymer has a ratio of about 20 wt % to about 80 wt %.

8. The pump of claim 7, wherein the blend of the crosslinked fluoropolymer and the non-crosslinked fluoropolymer has a ratio of about 30 wt % to about 70 wt %.

9. The pump of claim 8, wherein the blend of the crosslinked fluoropolymer and the non-crosslinked fluoropolymer has a ratio of about 50 wt % to about 50 wt %.

10. The pump of claim 6, wherein the non-crosslinked fluoropolymer comprises polytetrafluoroethylene, modified polytetrafluoroethylene, fluorinated ethylene propylene (FEP), poly tetrafluoroethylene-perfluoropropylvinylether (PFA), or combinations thereof.

11. The pump of claim 1, wherein the material comprises filler at about 0 wt % to about 50 wt % of the total weight of the material.

12. The pump of claim 1, wherein the material is substantially free of filler.

13. The pump of claim 1, wherein the seal substantially prevents leaks at a pressure of up to about 120 MPa at variable flow rates.

14. The pump of claim 1, wherein the pump is a high pressure liquid chromatography pump.

* * * * *